US009888882B2

United States Patent
Wu et al.

(10) Patent No.: US 9,888,882 B2
(45) Date of Patent: Feb. 13, 2018

(54) METHOD OF BRAIN WAVE ANALYSIS (71) Applicant: Taiwan Advanced Sterilization Technology, Inc., Taichung (TW)

(72) Inventors: Peng-Chieh Wu, Taipei (TW);
Wen-Hsuan Liao, Taichung (TW);
Wei-Hsuan Liao, Taichung (TW);
Yung-Ting Kuo, Taipei (TW)

(73) Assignee: Taiwan Advanced Sterilization Technology, Inc., Taichung (TW)

( * ) Notice: Subject to any disclaimer, the term of this patent is extended or adjusted under 35 U.S.C. 154(b) by 841 days.

(21) Appl. No.: 14/221,599

(22) Filed: Mar. 21, 2014

(65) Prior Publication Data
US 2014/0296731 A1 Oct. 2, 2014

(30) Foreign Application Priority Data

Mar. 28, 2013 (TW) .............................. 102111152 A (51) Int. Cl.
*A61B 5/02* (2006.01)
*A61B 5/00* (2006.01)
*A61B 5/0484* (2006.01)
*A61B 5/16* (2006.01)

(52) U.S. Cl.
CPC .......... *A61B 5/7203* (2013.01); *A61B 5/0484* (2013.01); *A61B 5/4064* (2013.01); *A61B 5/7278* (2013.01); *A61B 5/162* (2013.01)

(58) Field of Classification Search
CPC ............................ A61B 5/0476; A61B 5/0482
See application file for complete search history.

(56) References Cited

U.S. PATENT DOCUMENTS 4,883,067 A * 11/1989 Knispel ................ A61B 5/0482
600/28
6,416,471 B1 * 7/2002 Kumar .................. G06F 19/323
128/903

(Continued)

FOREIGN PATENT DOCUMENTS

CN 101584582 A 11/2009
TW 201025857 A1 7/2010

(Continued)

OTHER PUBLICATIONS

"Dynamic imaging of coherent sources Studying neural interactions in the human brain" by Gross et al., PNAS, vol. 98, No. 2, Jan. 16, 2001.*

(Continued)

*Primary Examiner* — Patricia Mallari
*Assistant Examiner* — Vasuda Ramachandran
(74) *Attorney, Agent, or Firm* — Haug Partners LLP (57) ABSTRACT

A method of brain wave analysis is to be implemented using a brain wave measuring instrument and a medical device. The method includes transmitting a nerve stimulation signal to cerebrum of a patient, measuring the nerve stimulation signal through the body of the patient so as to obtain discharge time information, measuring a brain wave signal from a head portion of the patient, obtaining energy distribution information according to the brain wave signal, and calculating behavior information according to the discharge time information and the energy distribution information.

10 Claims, 6 Drawing Sheets

(56) References Cited

U.S. PATENT DOCUMENTS

| | | | |
|---|---|---|---|
| 6,690,974 B2* | 2/2004 | Archer | A61N 1/36064 607/45 |
| 2001/0029391 A1* | 10/2001 | Gluckman | A61N 1/36014 607/2 |
| 2007/0038382 A1* | 2/2007 | Keenan | A61B 5/117 702/19 |
| 2010/0057159 A1* | 3/2010 | Lozano | A61N 1/36096 607/45 |

FOREIGN PATENT DOCUMENTS

| | | |
|---|---|---|
| TW | 201034624 A1 | 10/2010 |
| TW | M425675 U1 | 4/2012 |
| TW | 201236673 A1 | 9/2012 |

OTHER PUBLICATIONS

Search Report issued in corresponding Taiwanese Application No. 102111152 dated Apr. 27, 2015 and its English Translation.

* cited by examiner

METHOD OF BRAIN WAVE ANALYSIS

CROSS-REFERENCE TO RELATED APPLICATION

This application claims priority of Taiwanese application no. 102111152, filed on Mar. 28, 2013.

BACKGROUND OF THE INVENTION

1. Field of the Invention

The present invention relates to a method of brain wave analysis to be implemented using a brain wave measuring instrument and a medical device.

2. Description of the Related Art

Instruments for brain disease treatment can be categorized as invasive and non-invasive products. Non-invasive products such as orally administered pills and invasive products such as Vagus Nerve Stimulation (VNS) are commonly seen.

In general, a brain wave measuring instrument usually measures only electroencephalograph (EEG) and electrocardiography (EKG) that are to be used for analysis and determination. However, when the brain wave measuring instrument is used in combination with an invasive product, a brain wave signal thus measured is accompanied by an interference signal that interferes with the brain wave signal, and the effect of the interference signal is usually overlooked. As such, the analysis is performed on the brain wave signal that is accompanied by the interference signal, which may possibly lead to misjudgment during treatment due to errors in the brain wave analysis.

SUMMARY OF THE INVENTION

The object of the present invention is to provide a method of brain wave analysis to be implemented using a brain wave measuring instrument and a medical device. The medical device is configured to be implanted into a body of a patient for connection to cerebrum of the patient via nerves of the patient.

The method includes the following steps:

A) transmitting, using the medical device, a nerve stimulation signal to the cerebrum of the patient;

B) measuring, using the brain wave measuring instrument, the nerve stimulation signal through the body of the patient so as to obtain discharge time information;

C) measuring, using the brain wave measuring instrument, a brain wave signal from a head portion of the patient;

D) obtaining, using the brain wave measuring instrument, energy distribution information according to the brain wave signal; and E) calculating, using the brain wave measuring instrument, behavior information according to the discharge time information and the energy distribution information.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
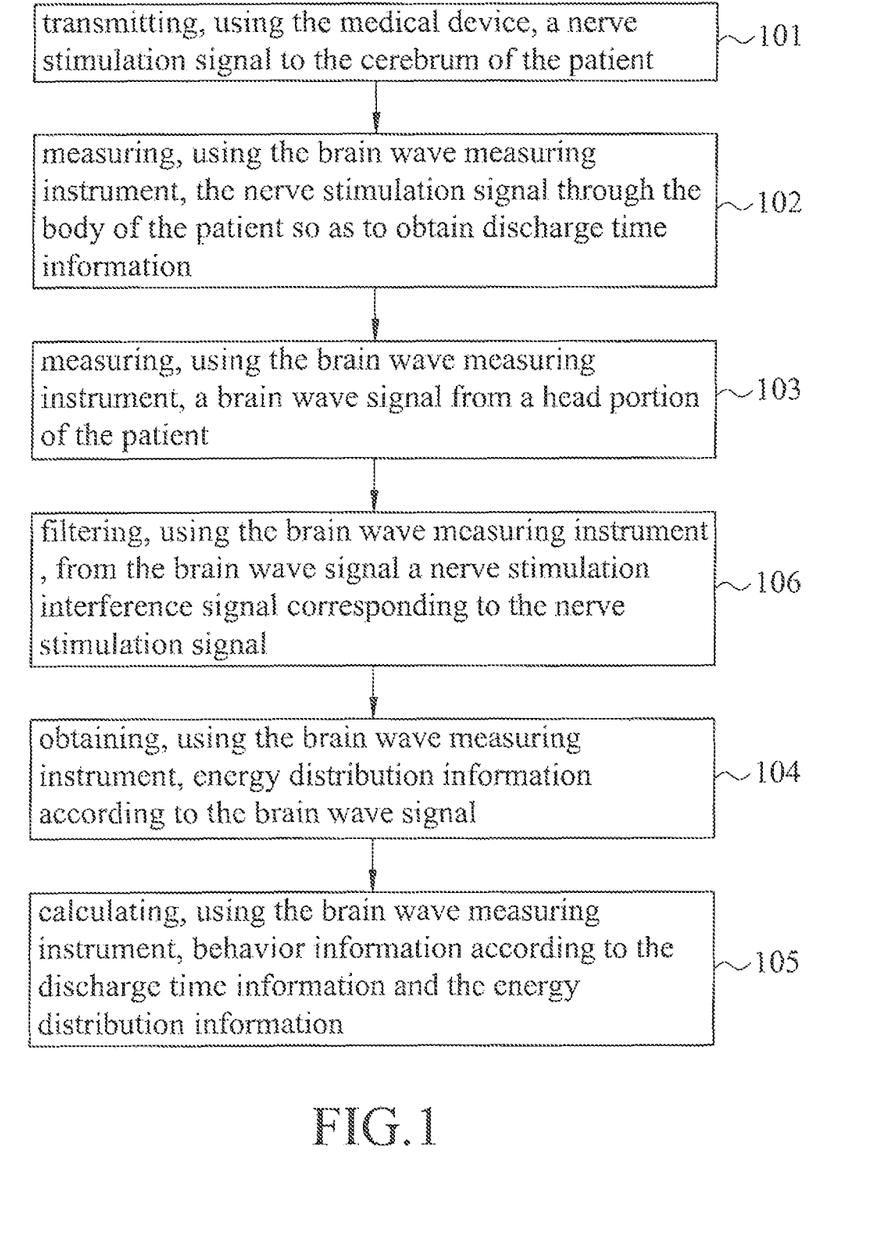
FIG. 1 is a flow chart illustrating the first preferred embodiment of the present invention.

Referring to FIG. 1, a method of brain wave analysis of a first preferred embodiment of the present invention is to be implemented using a brain wave measuring instrument and a medical device. The medical device is configured to be implanted subcutaneously into the left chest of the patient for connection to cerebrum of the patient via a wire that is tied to the nerves in the neck. The brain wave measuring instrument includes a plurality of pairs of electrodes that are attached to the skin of the patient. A pair of the electrodes is attached to the brain portion of the patient for measuring brain wave, and another pair is attached to the surface of the skin of the left side of the neck of the patient for measuring the signal produced by the medical device.

The process of the brain wave measuring instrument analyzing the brain wave signal according to a nerve stimulation signal will now be described in further detail in the succeeding paragraphs.

As illustrated in step 101 in FIG. 1, the medical device that is implanted transmits a nerve stimulation signal to the cerebrum of the patent. In this step, the nerve stimulation signal from the medical device is transmitted to the cerebrum of the patient through the wire and nerves, producing stimulation in the cerebrum.

As illustrated in step 102, the brain wave measuring instrument is used to measure the nerve stimulation signal through the body of the patient so as to obtain discharge time information. In this step, the brain wave measuring instrument measures the nerve stimulation signal via the pairs of electrodes attached on the skin of the patient to obtain the discharge time information. For instance, the medical device discharges for 30 seconds after each 30-second interval, and accordingly, the brain wave measuring instrument obtains a measurement of the medical device discharging from the $0^{th}$ to the $30^{th}$ seconds, non-discharging from the $30^{th}$ to the $60^{th}$ seconds, discharging from the $60^{th}$ seconds to the $90^{th}$ seconds, and so on.

As illustrated in step 103, the brain wave measuring instrument measures a brain wave signal produced from stimulation of the cerebrum, from the head of the patient via the pair of the electrodes attached to the brain portion of the patient.

As illustrated in step 106, the brain wave measuring instrument is used so filter from the brain wave signal a nerve stimulation interference signal corresponding to the nerve stimulation signal. The purpose of transmitting the nerve stimulation signal is to stimulate corresponding physiological reactions. However, the brain wave signal detected via the electrodes not only includes a signal that originates from the cerebrum, but also includes the nerve stimulation interference signal that results from the nerve stimulation signal, the latter of which is not needed for analysis. Therefore, in this step, the brain wave measuring instrument filters from the brain wave signal the nerve stimulation interference signal using a first filtering algorithm. The first filtering algorithm can be algorithms such as Independent Component Analysts (ICA), Principal Component Analysis (PCA), Projection Pursuit Principal Component Analysis (PPPCA), Factor Analysis (FA), Singular Value Decomposition (SVD), or other algorithms that can achieve the same filtering effect.

As illustrated in step 104, the brain wave measuring instrument is used to obtain energy distribution information according to the brain wave signal. The energy distribution information can be in the form of a three dimensional frequency spectrum chart, wherein X axis corresponds to time, Y axis corresponds to frequency and Z axis corresponds to energy, or can be a two dimensional frequency spectrum chart, wherein X axis corresponds to time, Y axis corresponds to frequency and energy is represented by colors. The energy distribution information can also be numerical data that shows, for any given time, the energy corresponding to a specific frequency.

As illustrated in step 105, the brain wave measuring instrument is used to calculate behavior information according to the discharge time information and the energy distribution information, which will be described in detail below.

In this preferred embodiment, the behavior information is an energy reference value. In step 105, a discharge region and a non-discharge region of the energy distribution information with reference to the discharge time information is first defined. According to the above-mentioned example, in which the medical device discharges from the $0^{th}$ to the $30^{th}$ seconds and non-discharges from the $30^{th}$ to the $60^{th}$ seconds, the discharge region can be defined from the $0^{th}$-$30^{th}$ seconds and the non-discharge region from the $30^{th}$ to the $60^{th}$ seconds.

Subsequently, the brain wave measuring instrument computes energy values of the discharge region and the non-discharge region, respectively, i.e., calculating a sum of the energy in the discharge region and that in the non-discharge region, respectively, to obtain the energy values of the discharge region and the non-discharge region, respectively. In this preferred embodiment, 3 Hz is used as a reference point, i.e., energies of frequencies larger than 3 Hz are summed to obtain the energy value. The reference point frequency is not limited to 3 Hz, and may be 2 Hz, 0 Hz etc., in other embodiments of this invention. For convenience, the energy value of the discharge region is defined as "On" and the energy value of the non-discharge region is defined as "Off".

Accordingly to the formula below, the brain wave measuring instrument calculates the energy reference value based on the energy values of the discharge region and the non-discharge region.

$$D = \frac{\text{Off} - \text{On}}{\text{Off}}$$

D represents the energy reference value. When the energy value (On) of the discharge region approaches the energy value (Off) of the non-discharge region, the energy reference value approaches zero. In other words, the brain wave energy behaves similarly during discharging and non-discharging of the medical device, i.e., the cerebrum being stimulated or not. Such result implies that parameters set in the medical device implanted in the patient are suitable for the patient.

In step 105, the brain wave measuring instrument can also calculate behavior information having a first energy reference value and a second energy reference value according to the discharge time information and the energy distribution information. The brain wave measuring instrument first defines a first non-discharge region, a discharge region subsequent to the first non-discharge region, and a second non-discharge region subsequent to the first non-discharge region and the discharge region of the energy distribution information with reference to the discharge time information. The brain wave measuring instrument then calculates energy values of the first non-discharge region, the discharge region and the second non-discharge region. Finally, the brain wave measuring instrument calculates a first energy reference value based on the energy values of the discharge region and the first non-discharge region, and calculates a second energy reference value based on the energy values of the discharger region and the second non-discharge region.

The formulas used herein are $$D\_1 = \frac{\text{Off}\_1 - \text{On}}{\text{Off}\_1} \text{ and } D\_2 = \frac{\text{Off}\_2 - \text{On}}{\text{Off}\_2}.$$

"D_1" and "D_2" represent the first energy reference value and the second energy reference value, respectively, "Off_1" and "Off_2" represent the energy values of the first non-discharge region and the second non-discharge region, respectively, and "On" represents the energy value of the discharge region. In terms of the timing, the discharge region is between and adjacent to the first non-discharge region and the second non-discharge region. D_1 and D_2 can be used to determine whether parameters set in the medical device implanted in the patient are suitable for the patient, and also prevent inaccurate measurement results due to possible unknown environmental factors during the first non-discharge region and the second non-discharge region.

Figure 4:
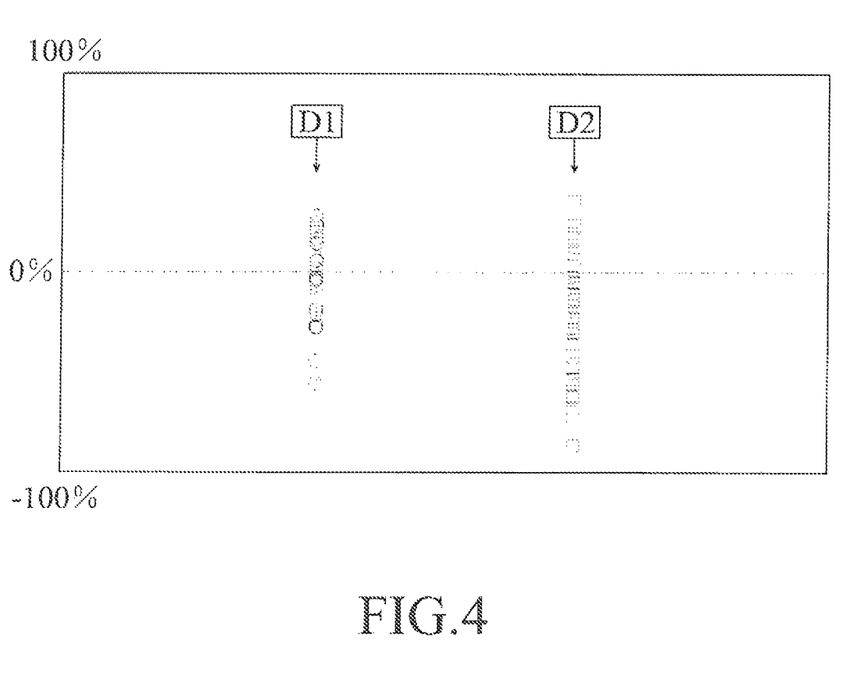
FIG. 4 shows a graph that illustrates energy reference values calculated with respect to various locations of the brain of a patient.

FIG. 4 shows a graph that illustrates values of D_1 (circular symbols) and D_2 (square symbols) with respect to various locations of the brain. This graph represents a clinical behavior of a patient having the medical device implanted lea treatment. A good clinical behavior will have symbols, converged towards the 0% value. The higher the degree of convergence, the more similar the brain wave energies behave during discharging and non-discharging of the medical device and the better the clinical behavior.

Figure 5:
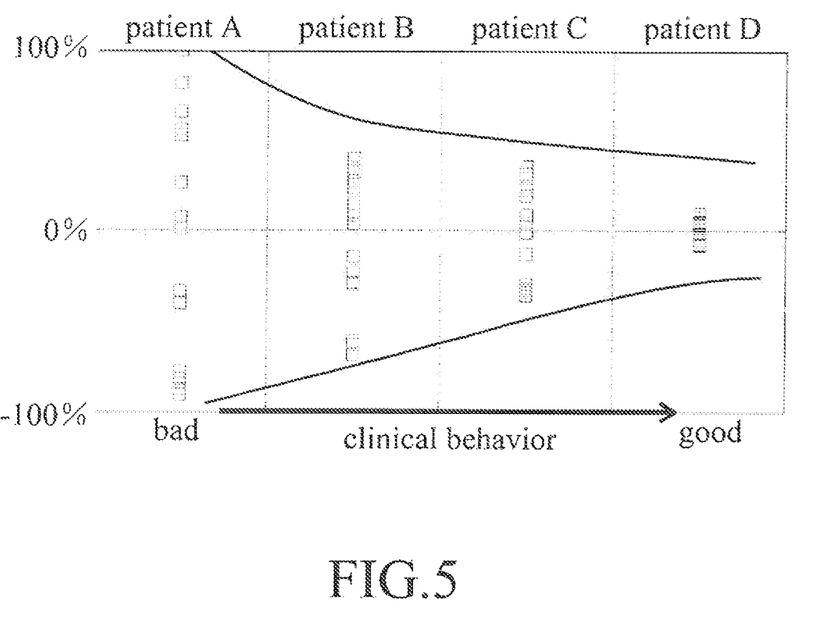
FIG. 5 shows energy reference values calculated for different patients A, B, C and C having different clinical behaviors.

The values of D_2 (square symbols) of patients A, B, C and D in FIG. 5 show that the clinical behavior of a patient A being the worst and that of the patient D being the best. From this information, whether parameters set in the medical device implanted in a particular patient are too high or low may be determined, and the parameters may accordingly be adjusted to become most suitable for a particular patient.

Figure 6:
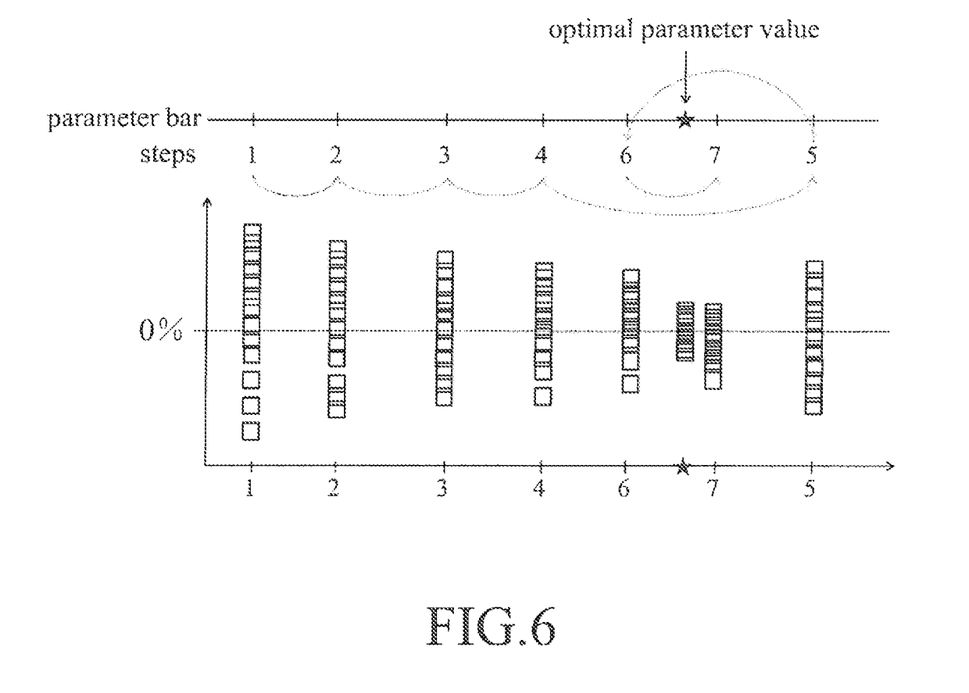
FIG. 6 illustrates a parameter adjustment process for optimizing operation of a medical device.

Referring to FIG. 6, when adjusting a parameter of a medical device implanted in a patient, the parameter is adjusted such that the values of D_2 (square symbols) approach the 0% value. Assuming that an optimal parameter value is represented by a star on a parameter value bar and in order to find that value, steps 1 to 7 are performed. As the parameter value is increased on the parameter bar, the values of D_2 converge towards the 0% value through steps 1 to 4 but diverge in step 5. Therefore, the parameter value is decreased in step 6 and again increased in step 7 such that the adjusted parameter approaches the optimal parameter value as represented by the star. Subsequently, more steps may be performed in order to fine-tune the parameter value to become the optimal parameter value.

Figure 2:
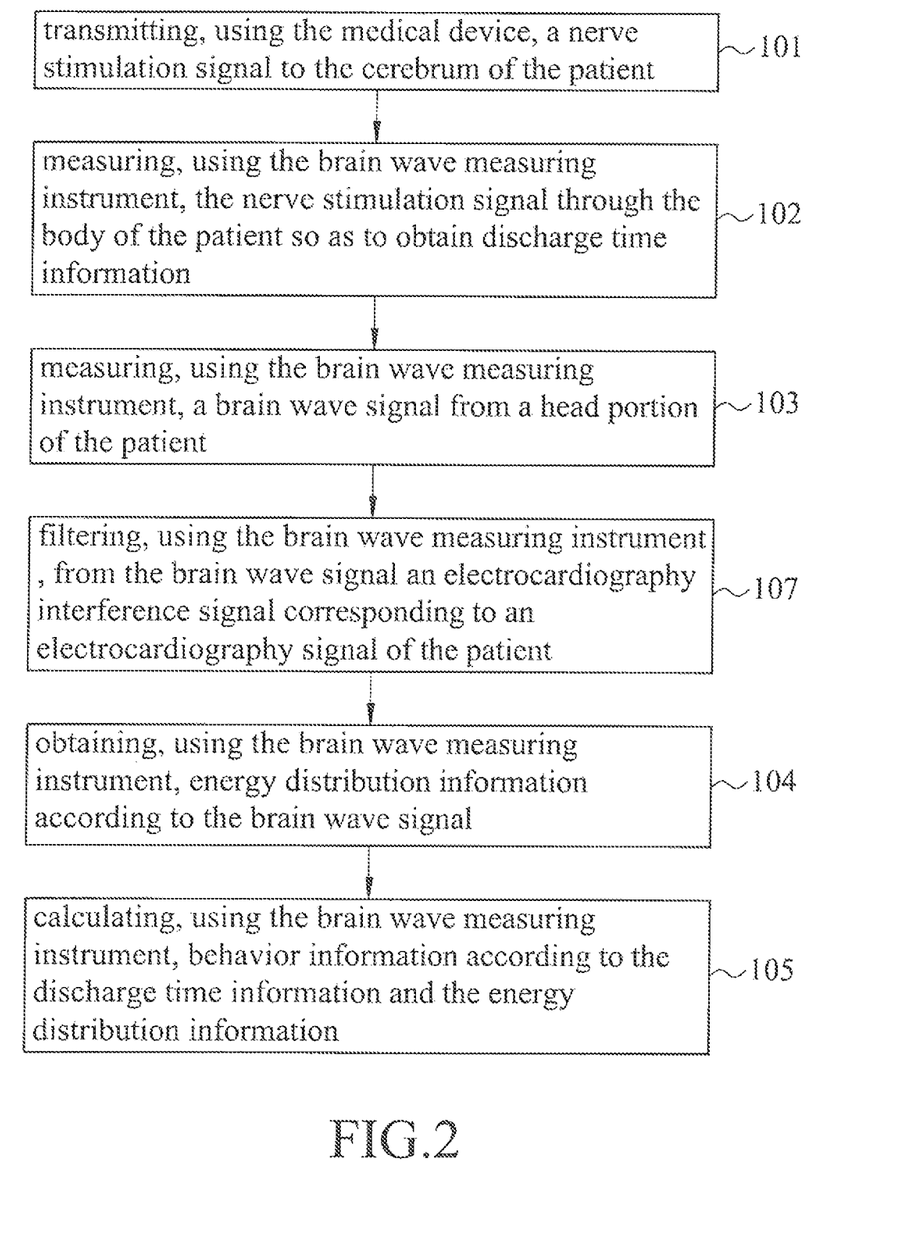
FIG. 2 is a flow chart illustrating the second preferred embodiment of the present invention.

Referring to FIG. 2, a second preferred embodiment the present invention differs from the first preferred embodiment in that there is a step 107 in between step 103 and step 104. The brain wave measuring instrument is used to filter from the brain wave signal an electrocardiography interference signal corresponding to an electrocardiography signal of the patient. In this step, the brain wave measuring instrument measures the electrocardiography signal of the patient via a pair of electrodes attached to the body of the patient, and then filters the electrocardiography interference signal from the brain wave signal using a second filtering algorithm. The second filtering algorithm can be algorithms such as Independent Component Analysis (ICA), Principal Component Analysis (PCA), Projection Pursuit Principal Component Analysis (PPPCA), Factor Analysis (FA), Singular Value Decomposition (SVD), or others algorithms that can achieve the same filtering effect.

Figure 3:
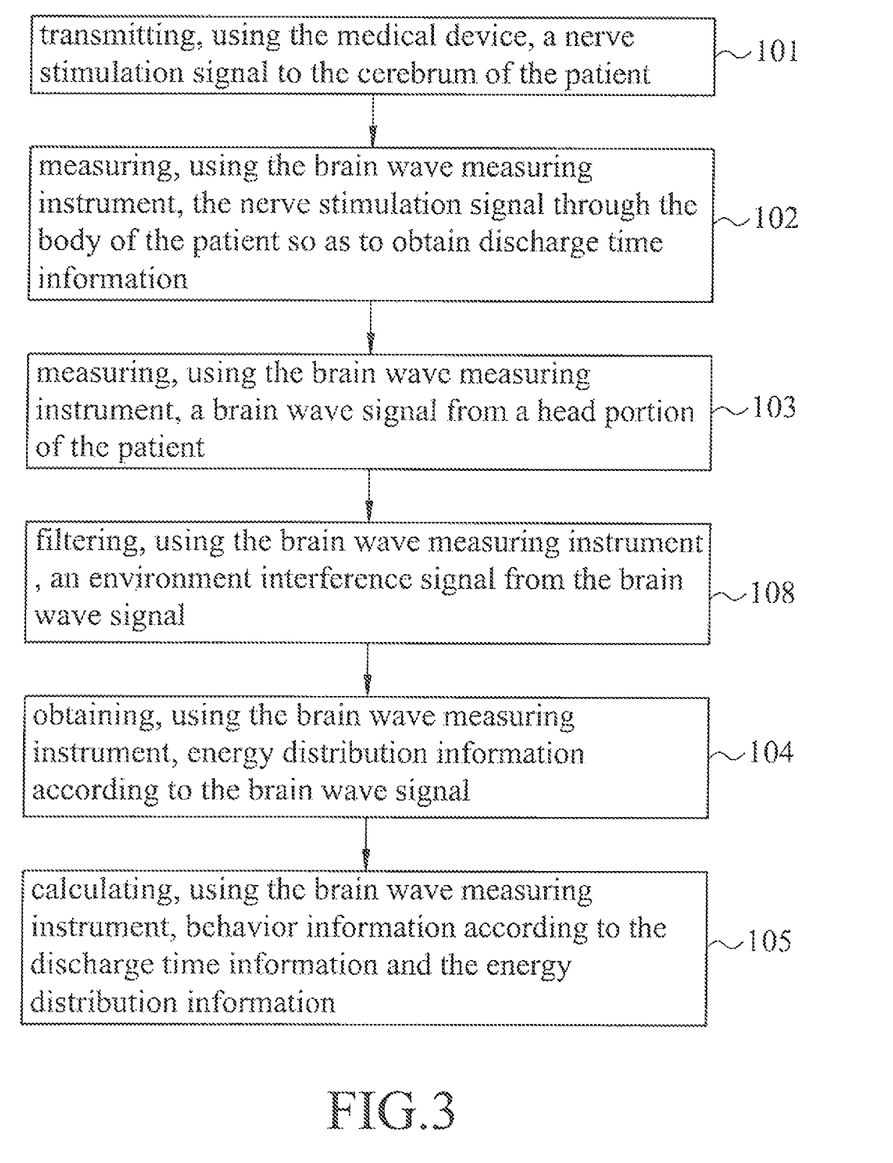
FIG. 3 is a flow chart illustrating the third preferred embodiment of the present invention.

Referring to FIG. 3, a third preferred embodiment of present invention differs from the first preferred embodiment in that there is a step 108 in between step 103 and step 104. The brain wave measuring instrument is used to filter from the brain wave signal an environment interference signal. In this step, the brain wave measuring instrument filters the environment interference signal from the brain wave signal using a third filtering algorithm. The environment interference signal could be 60 hz signals caused by alternating current noise, or specific frequencies used by cellular phones. Similarly, the third filtering algorithm can be algorithms such as Independent Component Analysis (ICA), Principal Component Analysis (PCA), Projection Pursuit Principal Component Analysis (PPCA), Factor Analysis (FA), Singular Value Decomposition (SVD), other algorithms that can achieve the same filtering effect. Alternatively, when the environment interference signal is within a specific frequency range, an appropriate filter can simply be used to filter out the environment interference signal.

It is worth mentioning that the first, second, and third filtering algorithms are not limited to be the same type of algorithm, and may be different from one another.

Moreover, any combination of steps 106, 107 and 108 may be inserted in between steps 103 and 104.

In summary, the present invention utilizes the brain wave measuring instrument to obtain discharge time information of the nerve stimulation signal, and through the aid of filtering algorithms, calculates behavior information in order to determine whether the parameters set in the medical device implanted in the patient are suitable for the patient.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method of brain wave analysis to be implemented using a brain wave measuring instrument and a medical device, the medical device being configured to be implanted into a body of a patient for connection to the cerebrum of the patient via nerves of the patient, the method comprising:
   A) transmitting, using the medical device, a nerve stimulation signal to the cerebrum of the patient;
   B) measuring, using the brain wave measuring instrument, the nerve stimulation signal through the body of the patient so as to obtain discharge time information;
   C) measuring, using the brain wave measuring instrument, a brain wave signal from a head portion of the patient;
   D) obtaining, using the brain wave measuring instrument, energy distribution information according to the brain wave signal; and
   E) calculating, using the brain wave measuring instrument, behavior information according to the discharge time information and the energy distribution information and adjusting parameters of the medical device that transmits the nerve stimulation signal according to the behavior information;
   wherein step E) includes:
   E-1) defining a discharge region and a non-discharge region of the energy distribution information with reference to the discharge time information;
   E-2) calculating energy values of the discharge region and the non-discharge region; and
   E-3) calculating an energy reference value of the behavior information based on the energy values of the discharge region and the non-discharge region.

2. A method of brain wave analysis to be implemented using a brain wave measuring instrument and a medical device, the medical device being configured to be implanted into a body of a patient for connection to the cerebrum of the patient via nerves of the patient, the method comprising:
   A) transmitting, using the medical device, a nerve stimulation signal to the cerebrum of the patient;
   B) measuring, using the brain wave measuring instrument, the nerve stimulation signal through the body of the patient so as to obtain discharge time information;
   C) measuring, using the brain wave measuring instrument, a brain wave signal from a head portion of the patient;
   D) obtaining, using the brain wave measuring instrument, energy distribution information according to the brain wave signal; and
   E) calculating, using the brain wave measuring instrument, behavior information according to the discharge time information and the energy distribution information and adjusting parameters of the medical device that transmits the nerve stimulation signal according to the behavior information;
   wherein step E) includes:
   E-1) defining a first non-discharge region, a discharge region subsequent to the first non-discharge region, and a second non-discharge region subsequent to the first non-discharge region and the discharge region of the energy distribution information with reference to the discharge time information;
   E-2) calculating energy values of the first non-discharge region, the discharge region and the second non-discharge region; and
   E-3) calculating a first energy reference value of the performance information based on the energy values of the discharge region and the first non-discharge region, and calculating a second energy reference value of the performance information based on the energy values of the discharge region and the second non-discharge region.

3. The method as claimed in claim 1, further comprising, between steps C) and D):
   F) filtering, using the brain wave measuring instrument, from the brain wave signal a nerve stimulation interference signal corresponding to the nerve stimulation signal.

4. The method as claimed in claim 1, further comprising, between steps C) and D):
   F) filtering, using the brain wave measuring instrument, from the brain wave signal an electrocardiography interference signal corresponding to an electrocardiography signal of the patient.

5. The method as claimed in claim 4, wherein step F) includes:
   F-1) measuring, using the brain wave measuring instrument, the electrocardiography signal from the body of the patient.

6. The method as claimed in claim 1, further comprising, between steps C) and D):
   F) filtering, using the brain wave measuring instrument, an environment interference signal from the brain wave signal.

7. The method as claimed in claim 2, further comprising, between steps C) and D):
   F) filtering, using the brain wave measuring instrument, from the brain wave signal a nerve stimulation interference signal corresponding to the nerve stimulation signal.

8. The method as claimed in claim 2, further comprising, between steps C) and D):
   F) filtering, using the brain wave measuring instrument, from the brain wave signal an electrocardiography interference signal corresponding to an electrocardiography signal of the patient.

9. The method as claimed in claim 8, wherein step F) includes:
   F-1) measuring, using the brain wave measuring instrument, the electrocardiography signal from the body of the patient.

10. The method as claimed in claim 2, further comprising, between steps C) and D):
    F) filtering, using the brain wave measuring instrument, an environment interference signal from the brain wave signal.

* * * * *